United States Patent [19]

Klein

[11] 4,162,674
[45] Jul. 31, 1979

[54] INSTRUMENT FOR RECORDING BLOOD PRESSURE

[75] Inventor: Johann Klein, Cologne, Fed. Rep. of Germany

[73] Assignee: Bayer Aktiengesellschaft, Leverkusen, Fed. Rep. of Germany

[21] Appl. No.: 857,962

[22] Filed: Dec. 6, 1977

[30] Foreign Application Priority Data

Dec. 18, 1976 [DE] Fed. Rep. of Germany ....... 2657612

[51] Int. Cl.$^2$ .......................... A61B 5/02; G01D 5/06
[52] U.S. Cl. ................................. 128/680; 346/33 ME
[58] Field of Search .................. 128/2.05 M, 2.05 A, 128/2.05 Q, 2.05 G; 346/33 ME, 33 D

[56] References Cited

U.S. PATENT DOCUMENTS

| 792,680 | 6/1905 | Taylor et al. | 346/33 D |
|---|---|---|---|
| 3,623,478 | 11/1971 | Saba | 128/2.05 Q |
| 3,969,734 | 7/1976 | Klein | 128/2.05 M |

*Primary Examiner*—George J. Marlo

*Attorney, Agent, or Firm*—Sprung, Felfe, Horn, Lynch & Kramer

[57] ABSTRACT

An electronic sphygmo-manometer utilizes a sleeve, which is wound around the patient's arm for taking pulse pressure values. The sleeve is equipped with a sound transducer connected to the pressure gauge. The point of the pressure gauge is deflectable perpendicular to the rotation plane and the needle tip can be brought into contact with a record card beneath the needle by means of an electro magnet. If the electro magnet is activated by a power circuit, which is controlled by an electrical signal created from the Korotkoff noise, the needle tip is pressed against the record card and produces an imprint on the record card. By sweeping the pressure from a value above the systolic pressure to a value below the diastolic pressure, a card is obtained with imprints covering the pressure range from the systolic to the diastolic value. The instrument is easily to be operated and provides for a high accuracy combined with low susceptibility to noise.

7 Claims, 1 Drawing Figure

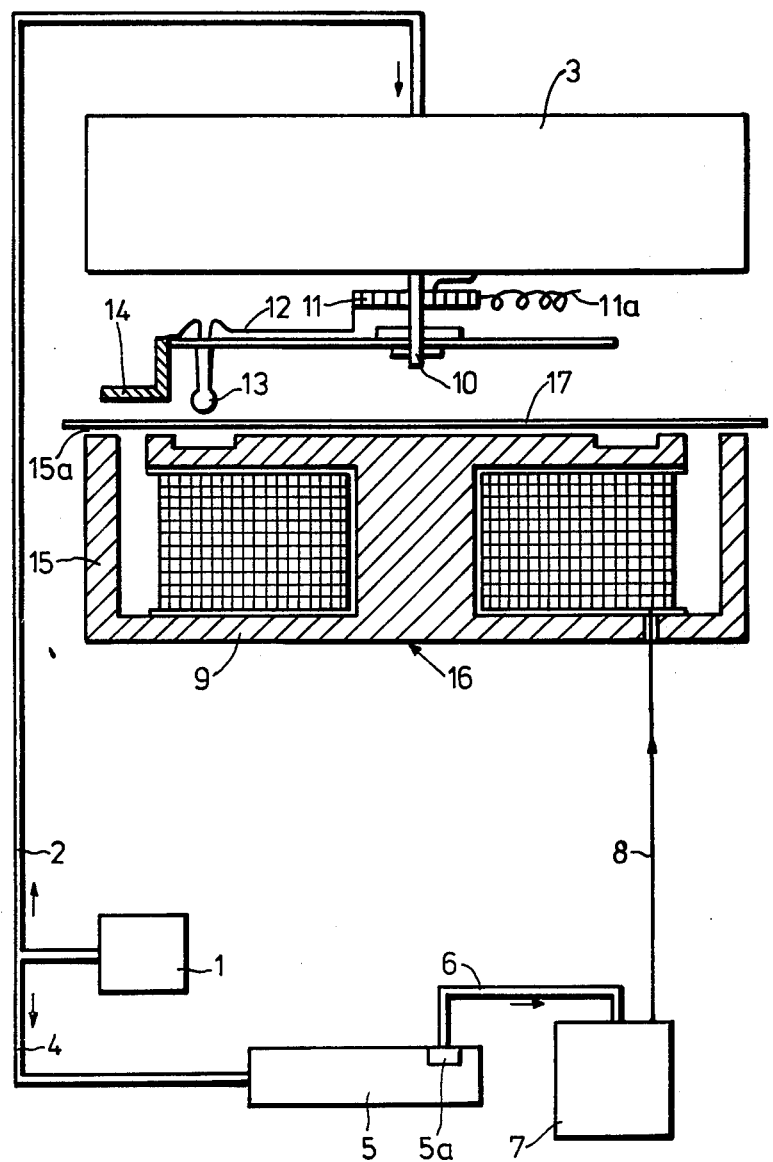

INSTRUMENT FOR RECORDING BLOOD PRESSURE

The invention relates to an instrument for recording blood pressure which displays the pulse pressure value taken on a patient by means of a sleeve, wherein the sleeve is connected to a sound transducer, which is in turn connected to an electrical monitoring unit for feeding the recorded movement on to a card, and to a pump and a pressure gauge having a moving needle, the needle moving in relation to the record card by means of the monitoring unit.

An instrument of this type for recording blood pressure is already known in which the pressure gauge has a pressure transducer with a torque producer which is adjustable approximately perpendicularly to the record support formed as a card. The torque producer is provided with a marking element which has a thermal pin. This thermal pin is connected to an electrical heating tube. The point of the thermal pin consists in known manner of a heat conductor (NYC conductor composed of a vitreous substance). The record card has a suitable coating and displays the corresponding measured pressure values, in particular in the case of measurement by the Riva-Rocci/Korotkoff method.

In this case the needle is fixed to a frame on which the transducer with bearing axles for the torque producer is fixed in stationary manner. Two pulling magnets are also fixed on the frame. The pulling magnets are activated by an electrical control current via the sound transducer so that at a predetermined moment the entire assembly is moved towards the record card. This is disadvantageous as it is necessary to move a relatively large mass consisting of the pressure gauge, the frame, the axle mounting, and the pulling magnets. Another disadvantage is that guides with narrow tolerances must be provided for the solenoids and/or the frame or other adjustable components. This leads to additional expense. However, if the operating tolerances are not held or the additional guide components not inserted accurately, the adjustable frame can be caused to jam. Additional space is required in at least one direction for the adjusting movement of the various components and this is also disadvantageous. Generally speaking, one guide is not sufficient and at least two guides are required for the frame. Guide pistons have to be lubricated if they are used as guide components. After a certain period of operation or when in use at lower temperatures, the lubricant sticks or becomes encrusted thus giving rise to problems in servicing or break-downs.

The object of the invention is to avoid the above disadvantages and to substantially simplify the instrument.

According to the invention, there is provided a blood pressure recording instrument for displaying pulse pressure values of a patient, comprising a sleeve for detecting the pulse pressure values, a sound transducer connected to the sleeve and cooperating with an electric monitoring unit for feeding the detected values on to a card, and a pump connected to the sleeve and to a pressure gauge having a movable needle which is mounted so as to be adjustable in relation to the record card by means of the monitoring unit, wherein the electric monitoring unit has an electro-magnet which is installed in stationary manner in the recording instrument, the record card is arranged directly above the pole faces of the electro-magnet and a pole piece composed of magnetisable material is provided on or near to the needle.

This gives a number of advantages. Only the needle with its magnetic pole piece is movable and thus the mass to be moved is reduced enormously. The vertical structural height may be reduced since the need for any guide elements for the electro-magnetic components, now fixed on a base plate or the like, is avoided. The dimensions in the horizontal direction or towards the side are reduced since pistons or guide elements are dispensed with. The expense involved in servicing is substantially reduced owing to the improved mechanical structure. An embodiment of the invention is shown in the accompanying drawing, which shows a diagrammatic arrangement of the basic components of the recording instrument wherein parts of the electrical control unit and the sound transducer are shown in sections.

The recording instrument comprises a pump 1 which communicates with a pressure gauge 3 via a first pneumatic connecting pipe 4. The sleeve has a pressure chamber (not shown) in known manner and is formed of a textile material. An acoustic chamber 5a may be provided in the sleeve. As an alternative to this preferred embodiment, the sleeve may also possess a microphone, in which case the recording instrument is constructed in a different manner. The sound chamber 5a communicates via a pneumatic connecting pipe 6 with a sound transducer 7, the structure of which is described in more detail in German Offenlegungsschrift No. 19 40 575.5. The sound transducer is connected via an electrical signal line 8 to at least one electric coil 9.

The pressure gauge may be a membrane manometer known per se. The measured pressure values are displayed by a needle 11 pivoted on a shaft 10. The needle 11 is adjustable in the vertical direction and has a needle arm 12, a needle point 13, and a pole piece 14 composed of magnetisable iron, for example soft iron. The pole piece is preferably angular, for example V-shaped or, as shown, L-shaped. The point of the needle is provided with a heating line 11a.

In a preferred embodiment the needle 11 comprises a reed, which is deflectable perpendicular to the needle rotation plane.

Opposite the pole piece 14, there is arranged at least one yoke 15 of a pot-shaped magnet 16 which may be electromagnetically activated by the coil 9. The yoke is preferably made of soft iron. The record card 17 is located directly above or on this pot-magnet and may be inserted via a gap, not shown in detail, and withdrawn again.

When the coil 9 is activated, the reed is deflected, so that the needle tip is pressed against the record card 17. The instrument functions in the following manner. The sleeve 5 is wound round the patient's *arteria brachialis* and can constrict or release this artery. The pressure in the pressure chamber of the sleeve is raised for this purpose via the primed pump 1 which is an electric pump or a manually operated rubber sheeting. The pulse signals in the patient's artery are transmitted to the sound chamber 5a which is relatively small compared to the pressure chamber and thence to the sound transducer 7. The associated pressure value is transmitted via the connecting pipe 2 to the pressure gauge and thus to the shaft 10 and the needle 12. During this process, the point of the needle 13 rotates in a plane perpendicular to the display plane above the measurement card 17 without touching the measurement card 17. It is now possible to visually determine and read the respective pressure values while the needle travels over the measured scale (not shown).

Now if the known Korotkoff noise is produced during further measurement (detectable either automatically in a loud speaker of the measuring instrument or by listening through a stethoscope) then the doctor can determine the systolic value on the record card by pressing a button. In an improved embodiment of the instrument, the Korotkoff noise is converted into an electric signal by an electrodynamic sound transducer (microphone). If this signal exceeds a predetermined threshold value, then the energising current for the coil 9 is triggered in the signal line 8. A magnetic field is thus formed between the pole faces thereof. This also applies to the front faces of the yoke 15 in whose magnetic field the pole piece 14 is magnetically polarised. By forming a pole and counter-pole between the face 15a and the pole piece 14, or optionally by means of other pole faces of the pot magnetic 16 with other pole pieces of the needle, the point of the needle 13 is drawn downwards on to the card 17 and is pressed down on to its surface at the moment when the systolic pressure value is produced. The heating line 11a is simultaneously connected. The record card is composed of a material which changes colour at relatively high temperatures. In this manner, the heated point of the needle 13 produces a coloured mark corresponding to that of the systolic pressure value on the record card 17.

The diastolic value which is given when the Korotkoff noise dies away may similarly be recorded on the card 17.

Independently of these two values, any pressure value which may be represented by the patient's pulse pressure may be determined in a similar manner by marking the card 17 and thus be used for example for filing purposes or transfer to another doctor (by manual or automatic insertion in the signal current in line 8).

What we claim is:

1. A blood pressure recording instrument for displaying pulse pressure values of a patient, comprising a sleeve for detecting the pulse pressure values, a sound transducer connected to the sleeve, an electric monitoring unit cooperative with the transducer for feeding the detected values on to a card, a pressure gauge having a movable needle which is mounted so as to be adjustable in relation to the record card by means of the monitoring unit and a pump connected to the sleeve and the pressure gauge, wherein the electric monitoring unit has an electromagnet which is installed in stationary manner in the recording instrument, the record card is arranged directly above the pole faces of the electro-magnet and a pole piece composed of magnetisable material is provided on or near to the needle.

2. An instrument according to claim 1, wherein the electro-magnet is pot-shaped with at least one yoke.

3. An instrument according to claim 2, wherein the said pole piece is angular and is mounted opposite the said yoke.

4. An instrument according to claim 3, wherein the pole piece is one of V or L-shaped.

5. An instrument according to claim 1, wherein the card lies on at least one pole face of the electro-magnet.

6. An instrument according to claim 1, further comprising means connecting the needle to a rotational shaft comprising an axially adjustable bearing whereby at least its arm is movable towards the card.

7. An instrument according to claim 1, wherein the needle has a resilient bearing comprising a metal spring which forms a conducting part for a heating line leading to the point of the needle.

* * * * *